(12) United States Patent
Tatsumi

(10) Patent No.: US 10,925,648 B2
(45) Date of Patent: Feb. 23, 2021

(54) VERTEBRAL FIXATION PLATE SYSTEM AND METHOD FOR USE

(71) Applicant: RLT Healthcare, LLC, Lake Oswego, OR (US)

(72) Inventor: Robert L. Tatsumi, Lake Oswego, OR (US)

(73) Assignee: RLT Healthcare, LLC, Lake Oswego, OR (US)

( * ) Notice: Subject to any disclaimer, the term of this patent is extended or adjusted under 35 U.S.C. 154(b) by 195 days.

(21) Appl. No.: 15/495,805

(22) Filed: Apr. 24, 2017

(65) Prior Publication Data

US 2017/0224389 A1    Aug. 10, 2017

Related U.S. Application Data

(63) Continuation-in-part of application No. 15/093,494, filed on Apr. 7, 2016, now Pat. No. 10,610,372.

(Continued)

(51) Int. Cl.
*A61B 17/70* (2006.01)
*A61F 2/44* (2006.01)
(Continued)

(52) U.S. Cl.
CPC ...... *A61B 17/7059* (2013.01); *A61B 17/8625* (2013.01); *A61F 2/447* (2013.01); *A61F 2/4455* (2013.01); *A61B 2576/00* (2013.01); *A61F 2002/3054* (2013.01); *A61F 2002/3093* (2013.01); *A61F 2002/30187* (2013.01); *A61F 2002/30331* (2013.01); *A61F 2002/30354* (2013.01); *A61F 2002/30367* (2013.01); *A61F 2002/30373* (2013.01); *A61F 2002/30433* (2013.01); *A61F 2002/30494* (2013.01); *A61F 2002/30553* (2013.01); *A61F 2002/30578* (2013.01); *A61F 2002/30593* (2013.01)

(58) Field of Classification Search
CPC ............. A61F 2002/30433; A61F 2002/30553
See application file for complete search history.

(56) References Cited

U.S. PATENT DOCUMENTS 5,041,113 A * 8/1991 Biedermann ...... A61B 17/7059
606/288
6,106,557 A * 8/2000 Robioneck ................ A61F 2/44
606/246

(Continued)

*Primary Examiner* — Samuel S Hanna
(74) *Attorney, Agent, or Firm* — Chernoff, Vilhauer, McClung & Stenzel, LLP

(57) ABSTRACT

A vertebral fixation plate system and a method for its use in a surgical procedure to fuse adjacent spinal vertebrae. A mounting member is attached to the vertebral fixation plate so that the fixation plate can move with respect to the mounting member through a range of available positions. The mounting member can be attached to a spinal interbody fusion device installed in place of a removed spinal disc, thus also loosely fastening the vertebral fixation plate to the fusion device. A fastener can tighten the vertebral fixation plate to the mounting member and establish a location of the vertebral fixation plate with respect to the vertebrae to be fused. Confronting surfaces of the mounting member and the vertebral fixation plate cooperate to keep the vertebral fixation plate in a desired location while it is fastened to the vertebrae being fused.

10 Claims, 13 Drawing Sheets

Related U.S. Application Data

(60) Provisional application No. 62/153,419, filed on Apr. 27, 2015, provisional application No. 62/144,225, filed on Apr. 7, 2015.

(51) Int. Cl.
*A61B 17/86* (2006.01)
*A61F 2/30* (2006.01)

(56) References Cited

U.S. PATENT DOCUMENTS

| | | | |
|---|---|---|---|
| 6,302,883 B1 * | 10/2001 | Bono | A61B 17/7058 606/291 |
| 8,690,928 B1 * | 4/2014 | Walkenhorst | A61B 17/7059 606/287 |
| 9,283,091 B2 * | 3/2016 | Melkent | A61F 2/4455 |
| 2007/0185489 A1 | 8/2007 | Abdou | |
| 2007/0270965 A1 | 11/2007 | Ferguson | |
| 2012/0041559 A1 * | 2/2012 | Melkent | A61F 2/4455 623/17.11 |
| 2012/0185048 A1 | 7/2012 | Phelps | |
| 2014/0107650 A1 | 4/2014 | Dacosta et al. | |
| 2015/0100089 A1 * | 4/2015 | Richelsoph | A61B 17/7091 606/246 |
| 2015/0320569 A1 | 11/2015 | Pisharodi | |
| 2016/0270924 A1 * | 9/2016 | Faulhaber | A61F 2/442 |
| 2016/0278815 A1 | 9/2016 | Fitzpatrick | |
| 2016/0367379 A1 | 12/2016 | Refai | |

* cited by examiner

VERTEBRAL FIXATION PLATE SYSTEM AND METHOD FOR USE

BACKGROUND OF THE INVENTION

The present invention relates to spine surgery and in particular relates to a vertebral fixation plate system and a method for its implantation and use in fusing vertebrae to one another.

It has long been known that one way to alleviate pain in patients who have suffered degeneration of spinal discs, so-called ruptured discs, is to remove the failed disc and replace it with an intervertebral support which can form a base for bone growth to fuse together the adjacent vertebrae. The conventional procedure for fusion of adjacent vertebrae involves insertion of a bone graft or an interbody fusion device between the vertebrae, together with implantation of a supporting intervertebral plate by screwing the plate to each of the involved vertebrae to immobilize the vertebrae with respect to each other while the bones become fused together.

It is desirable for the supporting plate, also called an intervertebral fixation plate, to be no larger than necessary to immobilize the affected vertebrae, since it may be necessary to fuse one of the affected vertebrae to an adjacent third vertebra. It may thus be important that the fixation plate not be so large as to prevent installation of another fixation plate adjacent to it. Additionally, it has been determined that when an intervertebral fixation plate extends close to a spinal disc the presence of the plate tends to lead to earlier failure of the nearby spinal disc.

Until recently, it has not been considered too important a factor that there is a significant amount of x-ray exposure involved in the way spinal fusion procedures have been performed. Recently, however, the importance of minimizing x-ray exposure, both for a patient and for medical personnel involved in such procedures, has been better appreciated.

It is also an important objective in performing spinal fusion procedures to minimize the invasiveness, including the amount of time required, of the entire surgical process, and to minimize the resulting trauma to the patient from the surgery itself, both by use of smaller incisions and by reducing the amount of time required to perform a procedure properly.

Conventional practice in implantation of vertebral fixation plates, at least in cervical spine fusion procedures, has been to expose the defective cervical disc to be removed, replace it with a bone graft or other interbody fusion device, place a vertebral fixation plate across the space between the vertebrae that are to be fused, in a position selected by the surgeon, and then, in most cases, secure the plate by installation of temporary fixation pins. Typically, a radiographic image is reviewed to determine whether the plate is in a satisfactory location. If necessary, the location of the plate may be adjusted, but it is desired to minimize the amount of radiation to which a patient and attending physicians are exposed, and so if an image shows the plate not to be located precisely where desired, an adjustment may be made without subsequent x-ray images being taken to evaluate the adjustment before the plate is permanently screwed to the involved vertebrae. There is no readily known way except through experience to quickly establish an initial optimum position for the vertebral fixation plate. Even an experienced surgeon may require a significant amount of time, up to 30 minutes or even more, to place and secure the vertebral fixation plate satisfactorily.

To fasten the plate to the involved vertebrae, the surgeon may manually hold the plate in the finally determined position while using a drill guide and drill to bore and tap holes in the vertebrae to receive screws to fasten the plate. Alternatively, self-tapping screws may be used once a bore has been made, or self-drilling screws may be utilized, but the position of the plate on the vertebrae, once chosen, is typically maintained manually by the surgeon, with the possible use of temporary fixation pins.

As a result, plates are often implanted in serviceable but less than optimal positions on patients' spinal vertebrae. Thereafter, when a medical care provider studies an x-ray photograph of the affected portion of the patient's spine, if the plate is not aligned completely parallel with the spine, or is located off-center, there may be some serious concern, even if the less-than-perfect location of the plate is completely adequate for securing and immobilizing the vertebrae as they become fused.

What is desired, then, is a spinal fixation plate system and a manner of installing it by which a surgeon can perform a spinal fusion procedure in a minimally invasive manner and in a minimum amount of time, and yet can place the plate in the optimum location with respect to the vertebrae being fused.

SUMMARY OF THE INVENTION

An implantable plate system for use in a procedure of fusing vertebrae in a patient is disclosed, along with a method for use thereof. In one version of an implantable plate system disclosed herein, as a principal aspect, an intervertebral graft body may have an attached reference member that may be called a base plate, a base disc, a base member, or a mounting member. A screw can attach the base to the intervertebral graft body while the plate is fastened to the vertebrae. An inner face of a vertebral fixation plate implant may define a recessed receptacle for the base member. The vertebral fixation plate thus fits closely against the base member with a limited amount of freedom to move with respect to the base member, once the graft body has been installed between the vertebrae to be fused but before the vertebral fixation plate is fastened to the vertebrae.

As one important aspect of the plate system disclosed herein, interactive mating portions of both the base and the plate can hold the plate in a selected one of several slightly different positions with respect to the base. Thus, the surgeon can install the graft body between vertebrae that are to be fused and can then, if necessary, attach the base to the graft body, and thereafter place the fixation plate in a position bridging the gap between the adjacent vertebrae in what appears to be an optimum location for the plate. The mating portions of the plate and the base will keep the plate in the selected location while that location is radiographically checked. If the radiographic image indicates that adjustment is necessary, the plate may then be moved to a better one of the positions available with respect to the base and retained in that adjusted position by the mating portions of the plate and the base while the plate is fastened to the vertebrae.

As one aspect of the system, a graft body may be manufactured with an integral base member so that it is unnecessary to install the base onto the graft body before the fixation plate is put into place.

In one embodiment of the system disclosed herein, the vertebral fixation plate defines an opening through which a portion of the base member and indicia on the base member may be seen.

As one aspect of the system disclosed herein, there may be a receptacle such as a bore defined in the base member to accept a retainer such as a screw extending into the graft body.

In one embodiment of the system, the base may include one or more projecting locators of a selected shape and size, and corresponding cavities may be provided in the receptacle portion of the fixation plate to receive the locators and hold the plate in a chosen one of several positions with respect to the base. Alternatively, the projecting locators may be present within the recessed receptacle in the inner face of the fixation plate, and corresponding cavities or indentations may be provided in the outer face of the base.

In one embodiment of the system, the several available positions in which the plate may be mated with the base may vary from one another with respect to an angle of rotation of the plate in a plane parallel with a central axis of the portion of the spine including the vertebrae being fused to each other.

In one embodiment of the system, the several available positions in which the plate may be mated with the base may vary from one another in terms of translation of the plate in a lateral or longitudinal direction with respect to the patient's spine.

In one embodiment of the system, an outer face of the vertebral fixation plate aligned with the receptacle for the base may include indicia visible to the surgeon when installing the plate. The position of the plate relative to the base may thus be easily discerned visually and the amount of adjustment of the position of the fixation plate relative to the base member may be seen and verified.

In another embodiment of the system, a mounting member may be attached to the intervertebral fixation plate and captured in a cavity defined in the side of the plate intended to face toward the graft body, so that the position of the intervertebral fixation plate with respect to the mounting member is adjustable until the fixation plate is fastened tightly to the graft body or the mounting member. Once the mounting member is attached to the graft body and a fastener is tightened to hold the vertebral fixation plate tightly to the mounting member the intervertebral fixation plate is kept immovable with respect to the vertebrae to be fused, maintaining the required position of the vertebral fixation plate while the plate is fastened to the adjacent vertebrae.

In yet another embodiment of the system, a mounting member may be located within a cavity defined in the side of the plate intended to face toward the graft body, and the mounting member is attached loosely to the plate. The mounting member may be attached tightly to the graft body after the graft body is placed between the vertebrae that are to be fused, thus attaching the intervertebral fixation plate to the graft body yet leaving some ability for the position of the plate to be adjusted. The location and orientation of the plate may then be adjusted with respect to the base member, after which the position of the plate with respect to the base member may be fixed. Screws may then be placed in the vertebrae to hold the plate in the desired position with respect to the vertebrae. Fasteners attaching the mounting member and the plate to the graft body may then be removed, leaving the vertebral fixation plate securely in place joining the vertebrae to each other.

In one embodiment, confronting surfaces of the captured base and the interior of the cavity in the vertebral fixation plate are shaped to interact with each other so as to prevent relative movement once the vertebral fixation plate is fastened tightly to the graft body.

A method for a spinal fusion procedure which is another aspect of the invention disclosed herein includes providing a base member attached to an intervertebral graft body; installing the graft body between a pair of vertebrae to be fused to one another; providing a vertebral fixation plate including a recessed receptacle for matingly receiving the base member; placing the fixation plate in a position spanning a space between the vertebrae to be fused together, with the base member received in the recessed receptacle in a selected one of a plurality of available relative positions; determining whether the fixation plate is in an optimum position with respect to the vertebrae to be fused together; moving the fixation plate, if necessary, to another one of the plurality of available positions relative to the base member; holding the fixation plate stationary with respect to the baseplate; and installing fasteners to secure the fixation plate to the vertebrae to be fused, thereby immobilizing the vertebrae with respect to each other.

A method for a spinal fusion procedure which is another aspect of the invention disclosed herein includes providing an intervertebral graft body; installing the graft body between a pair of vertebrae to be fused to one another; providing a vertebral fixation plate with a mounting member attached to the fixation plate and located within a recessed receptacle defined in the vertebral fixation plate; fastening the mounting member to the installed graft body, thereby placing the fixation plate in a position spanning a space between the vertebrae to be fused together; adjusting the position of the vertebral fixation plate with respect to the mounting member and tightening a fastener to fix the position of the plate with respect to the mounting member; determining whether the fixation plate is in an optimum position with respect to the vertebrae to be fused together; moving the fixation plate, if necessary, to another one of a plurality of available positions relative to the mounting member; holding the fixation plate stationary with respect to the mounting member; installing fasteners to secure the intervertebral fixation plate to the vertebrae to be fused, thereby immobilizing the vertebrae with respect to each other as they become fused together, and removing the fasteners attaching the plate and the mounting member to the graft body.

According to one embodiment of the method, the base, or mounting member, may be provided as an integral part of the intervertebral graft body, making it unnecessary to install and attach the base member to the graft body after the graft body has been placed between the vertebrae to be fused.

The foregoing and other objectives and features of the apparatus and method disclosed herein will be more readily understood upon consideration of the following detailed disclosure taken in conjunction with the accompanying drawings.

DETAILED DESCRIPTION OF PREFERRED EMBODIMENTS

Figure 1:
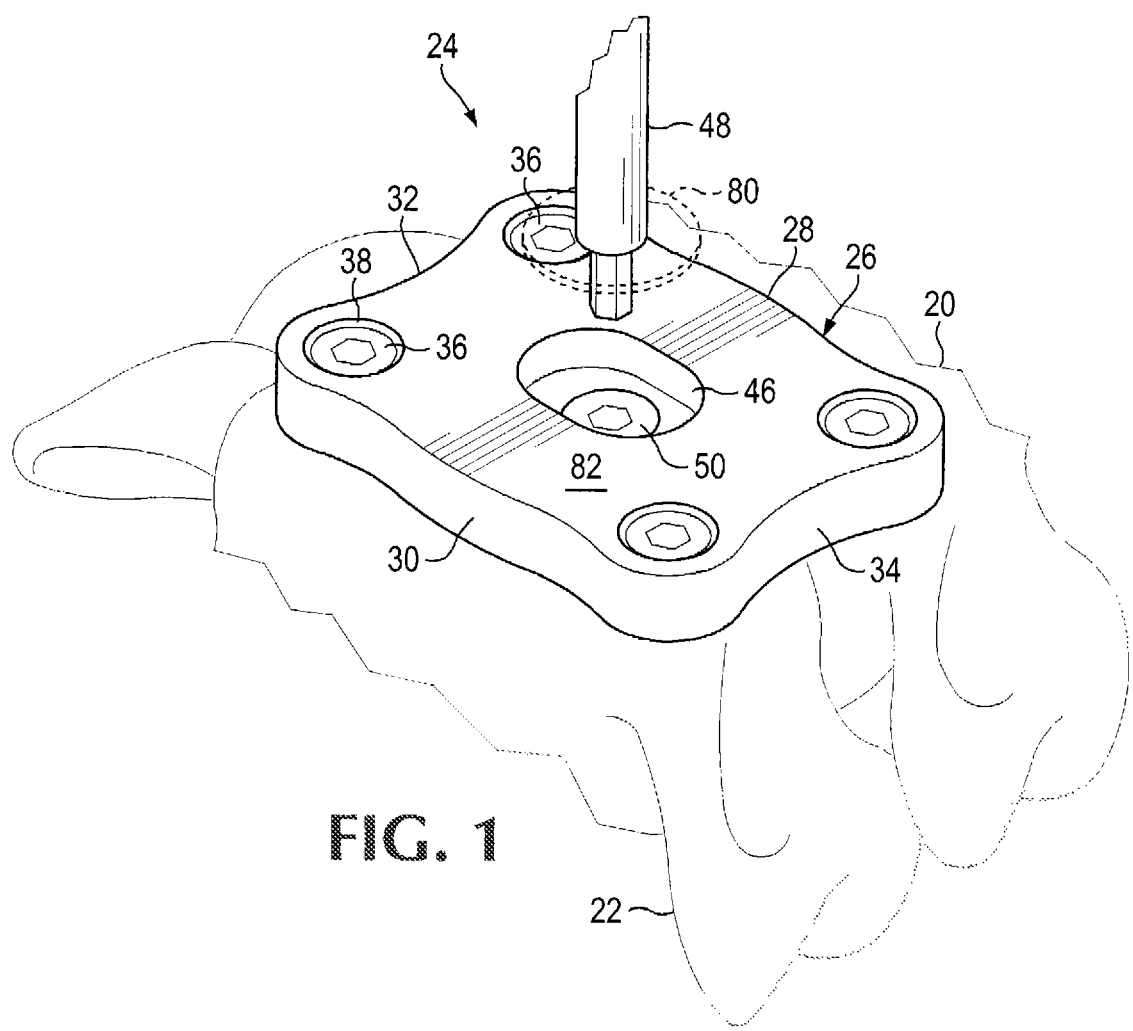
FIG. 1 is an isometric view of two cervical vertebrae of a person's spine, showing a vertebral fixation plate installed according to the present invention as part of a spinal fusion procedure.
Figure 2:
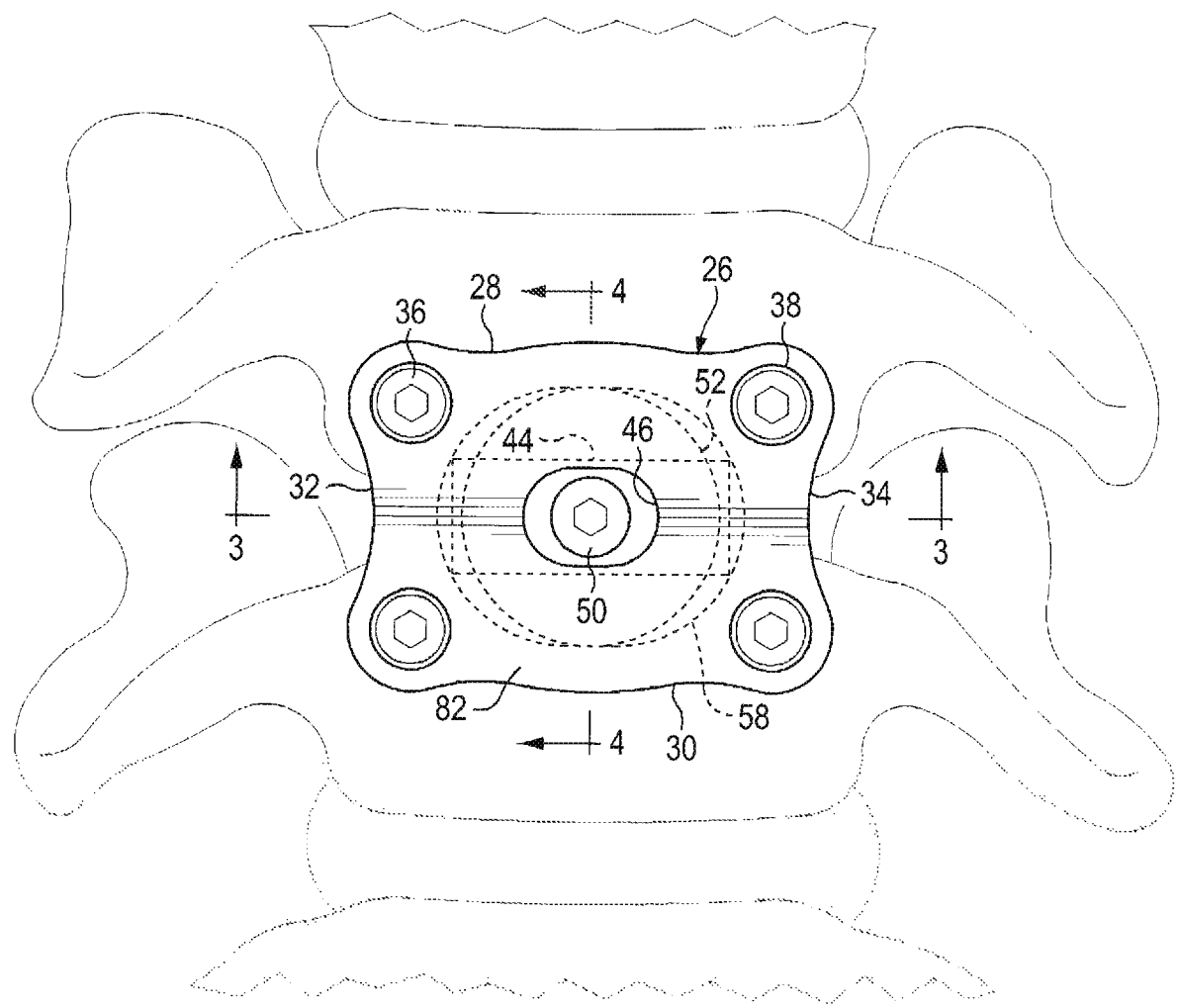
FIG. 2 is a plan view of the portion of a cervical spine shown in FIG. 1, showing the installed vertebral fixation plate.

Referring now to the drawings that form part of the disclosure herein, in FIGS. 1 and 2 a cervical portion of a spine including two adjacent vertebrae 20, 22 is shown with a vertebral fixation plate system 24 in place immobilizing the two vertebrae 20, 22 with respect to each other. A vertebral fixation plate 26 has a pair of opposite ends 28, 30, respectively facing in cephalad and caudal directions, and a pair of opposite lateral sides 32, 34. Fasteners such as screws 36 are mounted in respective receptacles 38 in the corners of the fixation plate 26, from which they extend through respective holes 40 in the fixation plate 26 into each of the vertebrae, as may be seen in FIGS. 3 and 4. A respective pair of the screws connect each of the opposite ends of the vertebral fixation plate to one of the vertebrae. Ideally, each of the ends, 28, 30 extends a short distance along the respective vertebra to which it is fastened, in order to leave room for an adjacent fixation plate (not shown) should a fusion be desired at the adjacent level of the spine at a later date.

Each of the receptacles 38 may be bowl-shaped, or approximately hemispherical, and the respective hole 40 associated with each receptacle 38 may be larger than the shaft of the screw 36 extending through the hole, so that the screw 36 may be oriented either perpendicular to the fixation plate 26 or at an angle α within a range of a few degrees from being perpendicular to the fixation plate 26. This can simplify installation of the screws 36 and allow each of the screws to be placed into a vertebra at a selected angle α intended to provide a secure attachment of the plate 26 to the vertebra concerned and to provide improved security by virtue of the screws 36 not being parallel with each other.

As with conventional vertebral fixation plates, the screws 36 used may be of any one of several different types, including screws for which bores must be tapped after being made, self-tapping screws, or self-drilling screws, at the election of the surgeon carrying out the spinal fusion procedure utilizing the vertebral fixation plate system 24 disclosed herein.

The vertebral fixation plate 26 bridges the space 42 from which the natural intervertebral disc has been removed from between the pair of adjacent vertebrae 20, 22 and where an interbody fusion device 44, hereinafter also called an intervertebral graft body, has been installed. In FIGS. 1-5, it may be seen that the vertebral fixation plate 26 defines a central opening 46 aligned with the graft body 44, and a tool 48 is shown aligned with, but spaced apart from a tool socket in the head of a fastener 50, which may be a screw, visible through the opening 46.

Figure 3:
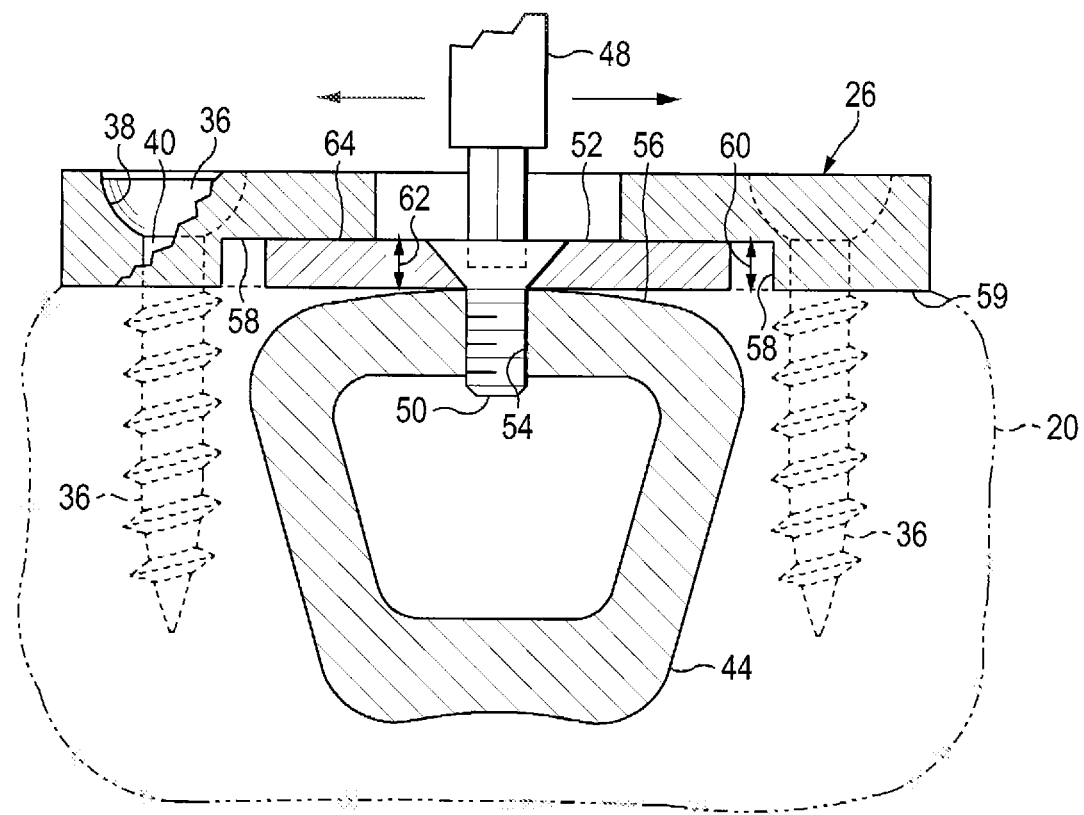
FIG. 3 is a sectional view taken along line 3-3 of FIG. 2.
Figure 4:
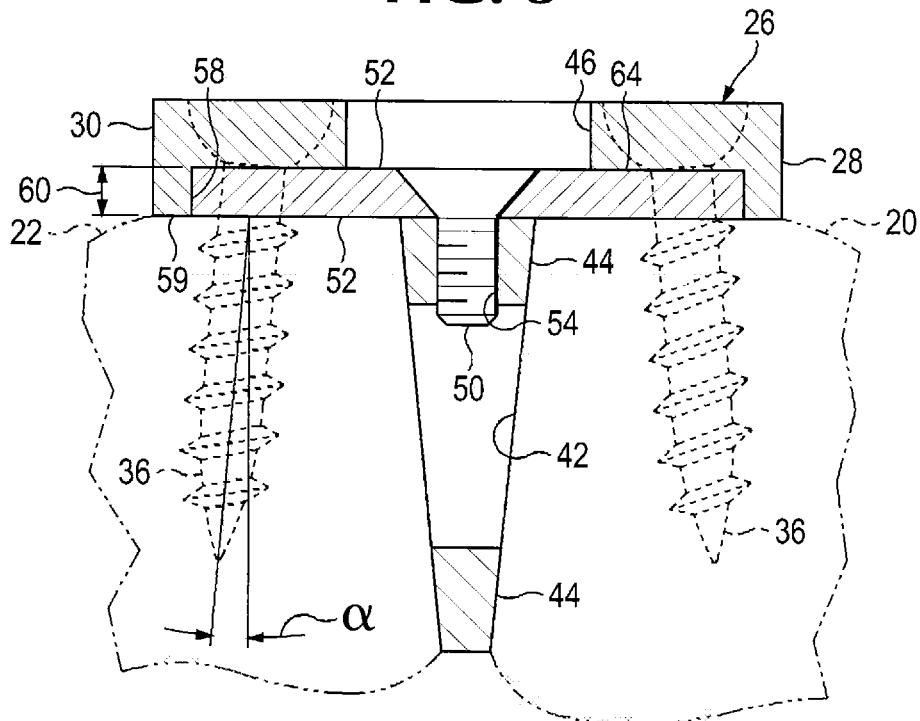
FIG. 4 is a sectional view taken along line 4-4 of FIG. 2.

As shown in FIGS. 3 and 4, the screw 50 visible in FIG. 1 is countersunk in a base member 52 and extends through the base member into a central bore 54 in an adjacent front face 56 of the intervertebral graft body 44, attaching the base member 52 to the intervertebral graft body 44. The base member 52 may have the form of a thin disc, and a corresponding receptacle 58 is provided in the form of a recessed opening defined in the inner side of the fixation plate. The receptacle may be a recess or cavity defined in the vertebral fixation plate 26 and have a depth 60 equal to the thickness 62 of the base member 52, for example slightly less than half the thickness of the vertebral fixation plate 26, so that the base member 52 will fit in and mate with the interior of the receptacle, as will now be explained.

Figure 5:
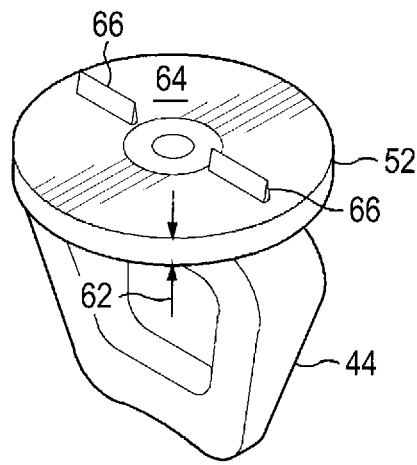
FIG. 5 is an isometric view, from a ventral and caudal viewpoint, showing an intervertebral graft body to which is attached a base member portion of a vertebral fixation plate system as disclosed herein.

An outer face 64 of the base member 52 may be provided with locators 66 in the form of small raised ridges as shown in FIG. 5. The recessed interior or ceiling face 68 of the receptacle 58, defined in the inner side 59 of the fixation plate to receive the base member 52 may be provided with corresponding locator cavities 70 such as grooves. The grooves can receive the locators 66 to keep the vertebral fixation plate 26 stationary with respect to the base member 52 until the vertebral fixation plate 26 has been fastened to the vertebrae by installation of the screws 36.

Figure 6:
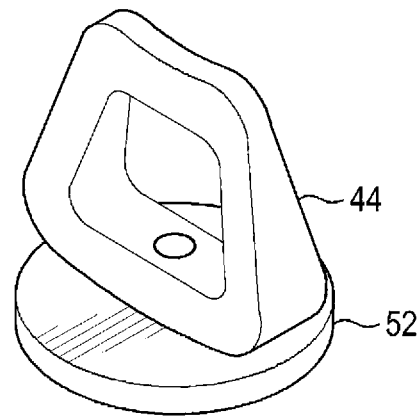
FIG. 6 is an isometric view of the intervertebral graft body and base member portion shown in FIG. 5, taken from the opposite direction.

As may be seen from an opposite viewpoint in FIG. 6, the base member 52 is attached to the intervertebral graft body 44, and is large enough to extend above and below the intervertebral space 42 where the graft body 44 would be installed between a pair of vertebrae 20, 22.

Figure 7:
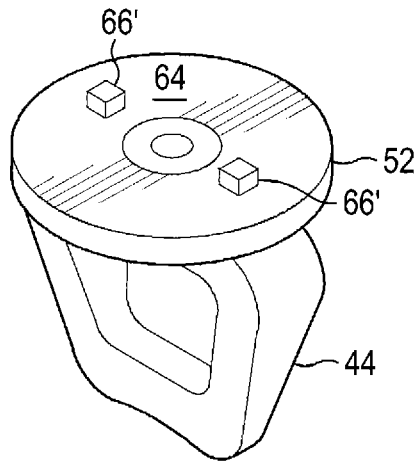
FIGS. 7-10 are isometric views, taken in a direction similar to that of FIG. 5, showing intervertebral graft bodies to which are attached base member portions of the vertebral fixation plate system disclosed herein and which are provided with respective different types of raised locator elements.
Figure 8:
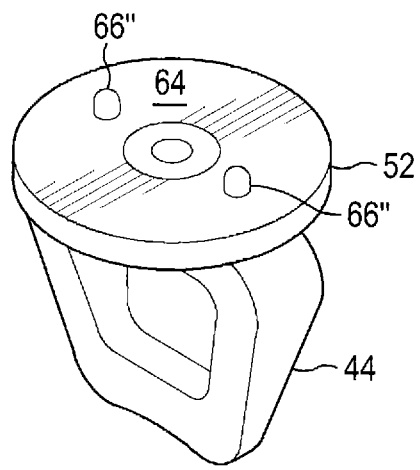
Figure 9:
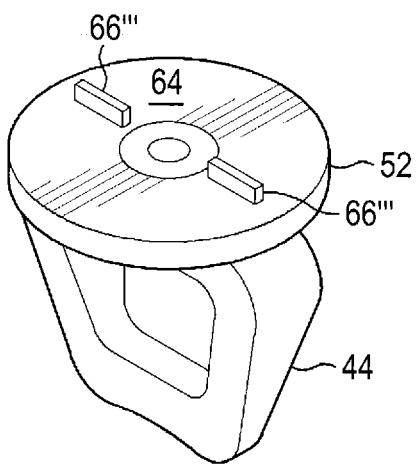
Figure 10:
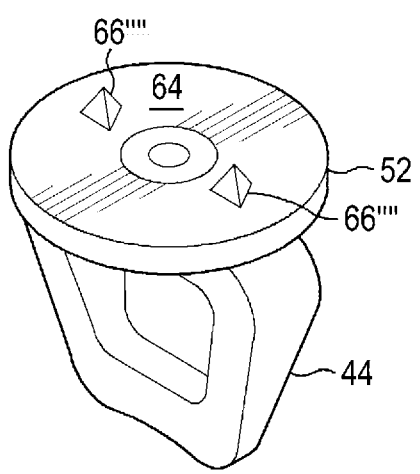

The outer face 64 of the base member, as shown in FIG. 5, is provided with small raised ridges as locators 66, but locators could be in any of several other forms, as well, such as the small cube-shaped locators 66' shown in FIG. 7, upwardly extending round-ended projections 66" as shown in FIG. 8, small radially-extending rectangular bars 66''', as shown in FIG. 9, or small pyramids 66'''' as shown in FIG. 10. Instead of the base members 52 attached to graft bodies 44 by a fastener, such as those shown in FIGS. 5-10, a base member 52 may be provided as an integral part of an interbody fusion device such as that shown in FIGS. 16 and 17.

A group of small locating cavities 70 with shapes and sizes corresponding to those of the locators 66, 66', etc. on a base member 52 are provided, closely spaced in the bottom, or ceiling, surface 68 of the receptacle 58 in the inner side 59 of a mating vertebral fixation plate. Appropriately located ones of the locating cavities 70 can receive the locators 66 with the vertebral fixation plate 26 in any of several slightly different available positions relative to the base member 52 with the base member 52 seated in the receptacle 58 in the inner side 59 of the vertebral fixation plate 26.

Figure 11:
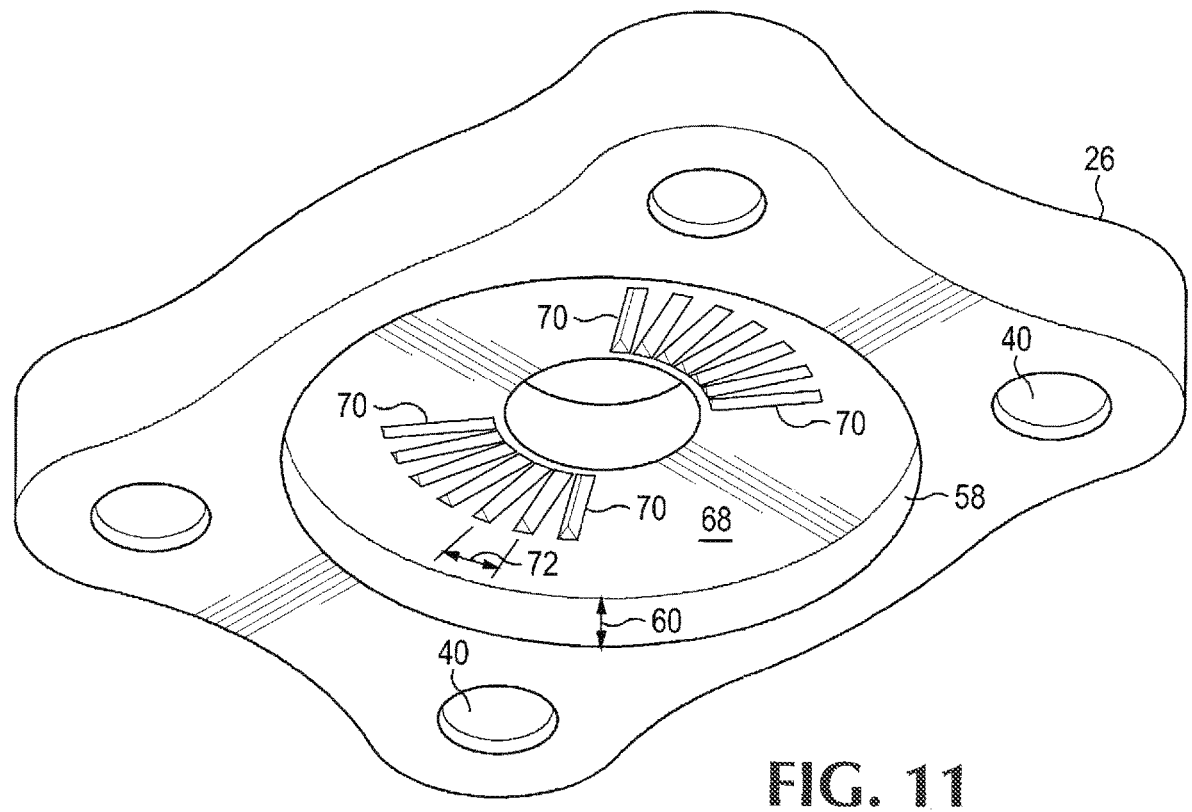
FIG. 11 is an isometric view showing the inner side of a vertebral fixation plate similar to that shown in FIGS. 1 and 2, and also showing a mating base member portion of the fixation plate system, similar to the base member portion shown in FIG. 5, facing toward a recessed receptacle defined in the inner face of the vertebral fixation plate.
Figure 11:
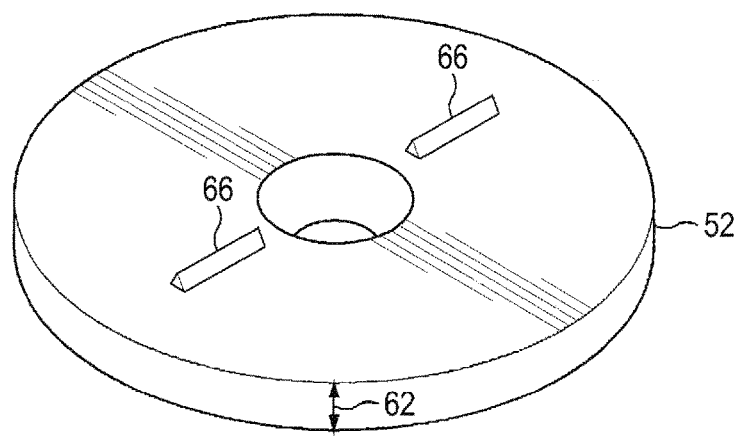
Figure 12:
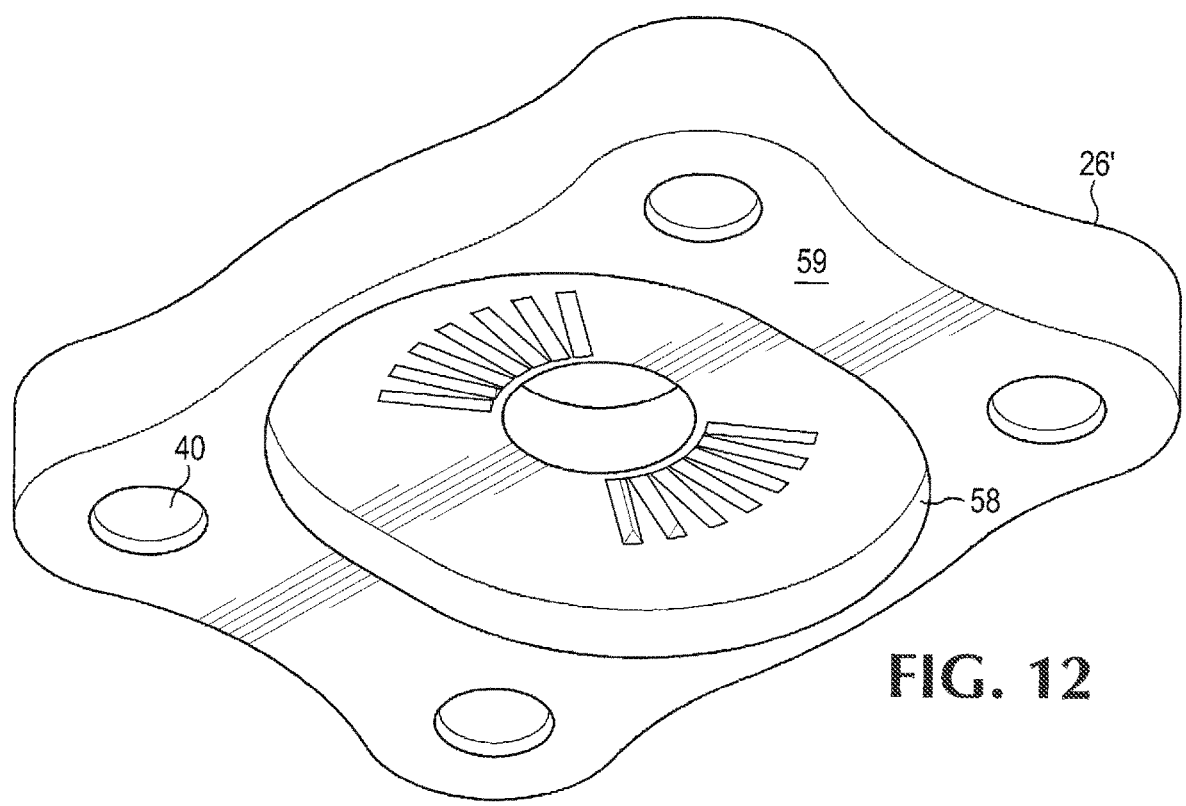
FIG. 12 is an isometric view showing the inner side of a vertebral fixation plate similar to that shown in FIG. 11, but with differently located receptacles for locator elements of a base member portion.
Figure 13:
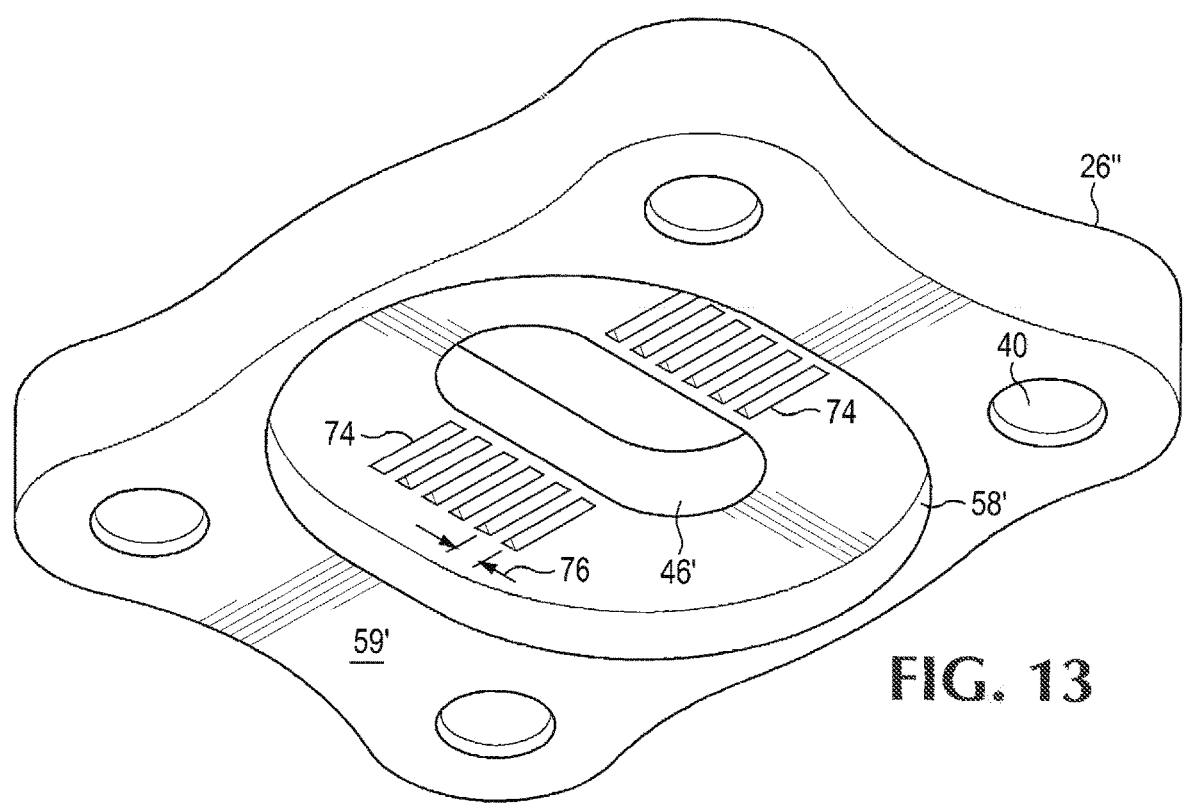
FIG. 13 is an isometric view showing the inner side of a vertebral fixation plate including receptacle grooves arranged parallel with one another and in which the plate includes an elongated central opening.
Figure 14:
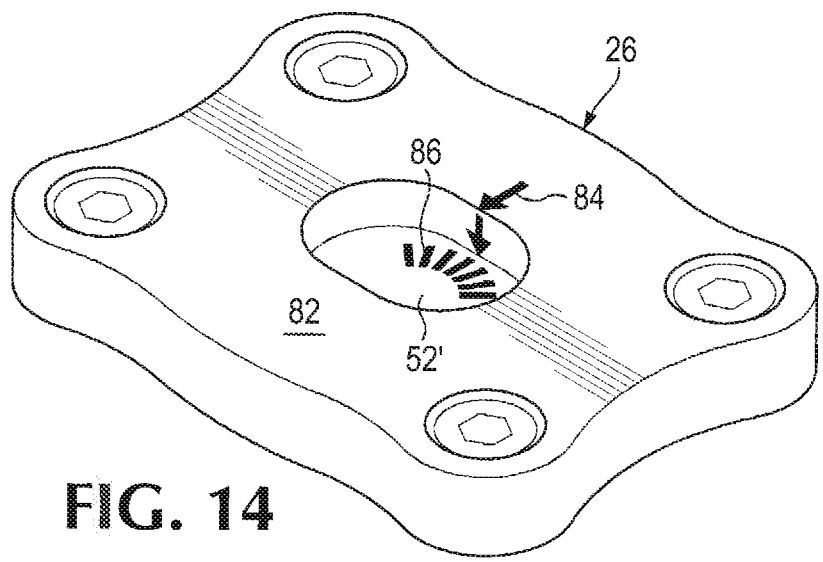
FIG. 14 is an isometric view showing the outer side of a vertebral fixation plate similar to that shown in FIG. 12, and on which there are indicia to show the position of the fixation plate relative to a base member portion of the plate system.
Figure 15:
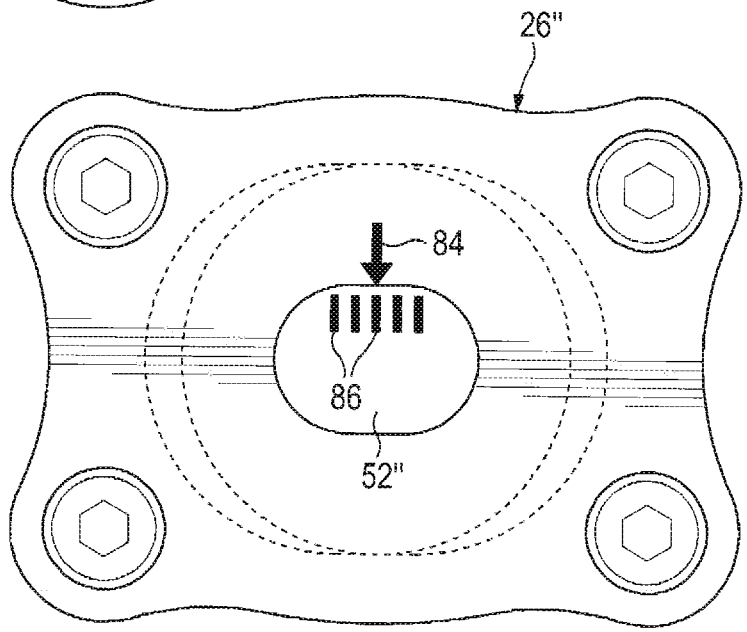
FIG. 15 is a plan view of a portion of a vertebral fixation plate assembly incorporating indicia on a vertebral fixation plate such as that shown in FIG. 14 and on the base member assembled with the vertebral fixation plate, for use in determining the position of the fixation plate relative to the base member.

For example, as shown in FIGS. 11 and 12, locating cavities 70 in the form of grooves may extend radially away from the central opening 46 in the vertebral fixation plate 26 and the location of the screw in the base plate member. The grooves may be spaced apart from each other by small angles 72, such as being separated from one another by intervals of, for example, 5° of rotation of the vertebral fixation plate 26 or 26' with respect to the base member 52, although smaller angular intervals might be used. in another version of the vertebral fixation plate 26", the central opening in the vertebral fixation plate may be an elongated hole 46', and grooves or other locating cavities 74 may be parallel with each other and spaced apart from one another by a small distance 76, such as 2 mm, to permit the location of the vertebral fixation plate 26" to be adjusted by translation with respect to the location of the base member 52. In that case, the recessed receptacle 58' defined by the inner side 59' of the vertebral fixation plate will be somewhat larger than the base member 52 leaving room for movement of the base member 52 relative to the interior of the receptacle 58', as shown in FIG. 3 and FIG. 13.

Figure 16:
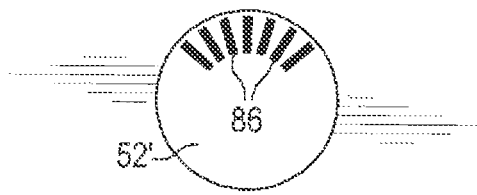
FIG. 16 is a plan view of a base member that may be included in the combination shown in FIG. 15.
Figure 17:
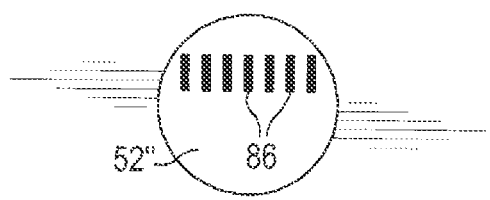
FIG. 17 is a plan view of a different base member useful as a part of a combination such as that shown in FIG. 15.

Referring now to FIGS. 14-17, in one embodiment of the vertebral fixation plate 26 the outer face 82 may include an arrow 84 or other indicia, and the base member 52' may also include indicia such as an engraved or otherwise visible mark 86 for each small angular interval of potential adjustment from a centrally aligned position of mating of the base member 52' with the corresponding vertebral fixation plate 26, as shown in FIG. 16. As shown in FIG. 17, the base member 52" may also include an engraved or other mark 86 for each small interval step of translation with respect to a corresponding vertebral fixation plate 26" providing for translation with respect to the base member as shown in the vertebral fixation plate 26" shown in FIG. 13.

Figure 18:
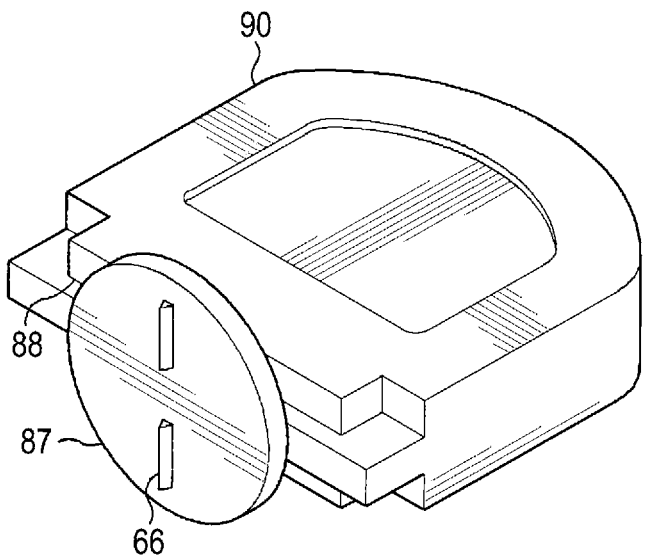
FIG. 18 is an isometric view of an interbody fusion device incorporating a base member for use as part of a vertebral fixation plate assembly according to the present disclosure.
Figure 19:
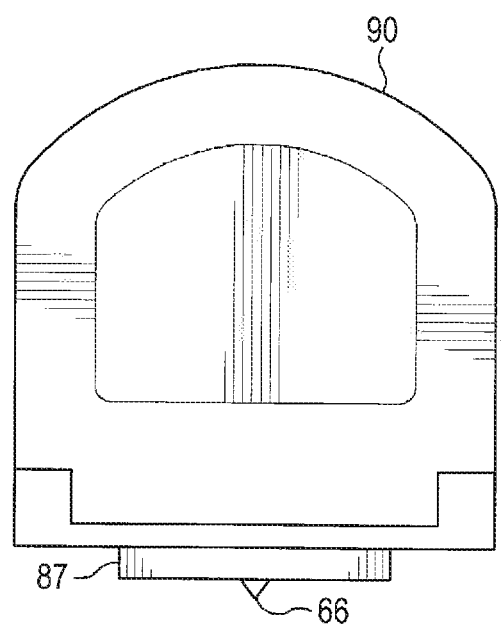
FIG. 19 is a plan view of the interbody fusion device shown in FIG. 18.
Figure 20:
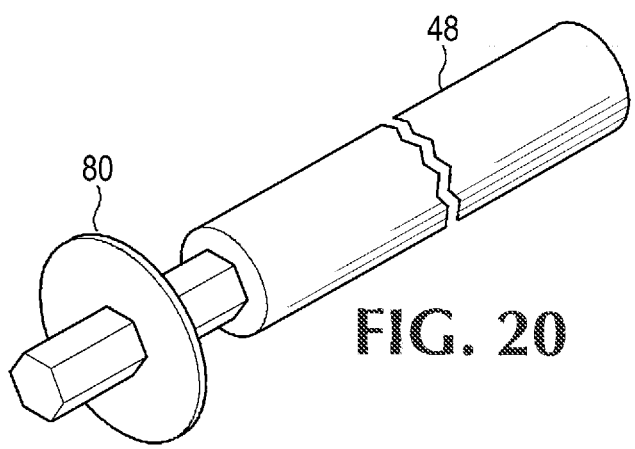
FIG. 20 is an isometric view of a tool for use in installation of a vertebral fixation plate together with a mounting member, or base, incorporated in or attached to an interbody fusion device.

While a suitable base member 52, made to mate with a particular vertebral fixation plate 26 or 26', etc., may be fastened to a conventional interbody fusion device or graft body 44, a shown in FIGS. 3-10, the base member may be integrated with an interbody fusion device or graft body 90, as shown in FIGS. 18 and 19. That is, a base member 87 may be a separate part made to fit into an appropriate slot 88 or other receptacle formed in a related graft body 90, which may be of a particular material intended to encourage and enhance fusion of the adjacent vertebrae 20, 22 after implantation. The base member 87 otherwise may be of a configuration similar to a base member 52 shown attached to a graft body in each of FIGS. 1-10, with one or more locators 66.

In order to quickly establish an optimum location for the vertebral fixation plate of the fixation plate system disclosed herein, a surgeon will make an incision leading to the patient's spine and will retract intervening tissue to gain access to the spine at the level where a disc is to be removed and the adjacent vertebrae are to be fused. The defective disc is removed and a graft body 44 is installed in its place. If the graft body is a conventional interbody fusion device as shown in FIGS. 3 and 4, a base member 52 is fastened to it by a fastener such as the screw 50, so that the result is as shown in FIGS. 1-10.

With the base member 52 exposed and overlapping, or at least not hidden between, the adjacent vertebrae 20, 22, the vertebral fixation plate 26 is placed atop the base member 52 or 87, so that the base member 52 extends into the recessed receptacle 58 in the inner side 59 of the vertebral fixation plate 26. The surgeon estimates the correct position for the vertebral fixation plate 26 and places the fixation plate against the vertebrae 20, 22 so that the base member 52 or 87 is received in the receptacle 58. Optionally, the surgeon may use a tool such as the tool shown 48 in FIG. 1, which may include a flange 80 that can be used to push against the outer face 82 of the vertebral fixation plate 26. Enough pressure is applied to cause the locator or locators 66 on the base member 52 or 87 to enter the closest available locating cavity 70 in the bottom or ceiling face 68 of the recessed receptacle 58, thus establishing an initial position for the vertebral fixation plate 26.

A radiographic image can then be obtained to determine whether the vertebral fixation plate 26 is in the desired location with respect to the vertebrae 20, 22 to which it is to be fastened. If an image suggests that a revised position is necessary, adjustment can be made in defined small steps in the desired direction, either angularly or in translation, depending upon the version of the fixation plate 26 and corresponding base member 52 being used. With marks 86 provided on the outer face 64 of the base member 87 and an arrow 84 on the outer face 82 of the vertebral fixation plate 26, as shown in FIGS. 16 and 17, the initial position of the fixation plate 26 relative to the base member 52 can be noted. The number of defined steps or intervals of movement needed can be determined from the image of the initial position, and the vertebral fixation plate 26 can be moved that distance to place the vertebral fixation plate 26 in an optimum position with respect to the base member 52, where the locators 66 will be received in the closest locator cavities 70, and the vertebral fixation plate 26 will be located optimally with respect to the vertebrae 20, 22 being fused.

The vertebral fixation plate 26 can then be held in that position, mated against the base member 52, by simple pressure, either using the tool 48 or by manual pressure exerted by the surgeon while the screws 36 are inserted into the receptacles 38 and through the associated holes 40 to fasten the vertebral fixation plate 26 to the vertebrae 20, 22 in a minimum amount of time. It may be most efficient to place a screw 36 into the vertebrae at each of a pair of diagonally opposite corners of the fixation plate 26 initially.

The definite retention of the vertebral fixation plate 26 in the chosen position, as a result of the mating of the locators 66 in the locator cavities 70 within the receptacle 58 defined in the inner side 59 of the vertebral fixation plate 26, gives the assurance that the vertebral fixation plate 26 will be located properly with respect to the space 42 between the vertebrae 20, 22 and as to alignment with the portion of the spine where vertebral fusion is to take place.

While the vertebral fixation plate system 24 disclosed above has addressed a single-level spinal fusion procedure, the system can similarly be used for fusion at one or more adjacent additional levels by utilizing a similar but longer vertebral fixation plate, long enough to extend to where it can be fastened to each of the involved vertebrae and including a recessed receptacle 58 to be mated with a base member 52 attached to a graft body 44 or incorporated in a graft body 90 implanted in the intervertebral space 42 at one of the levels where fusion is to take place.

Figure 21:
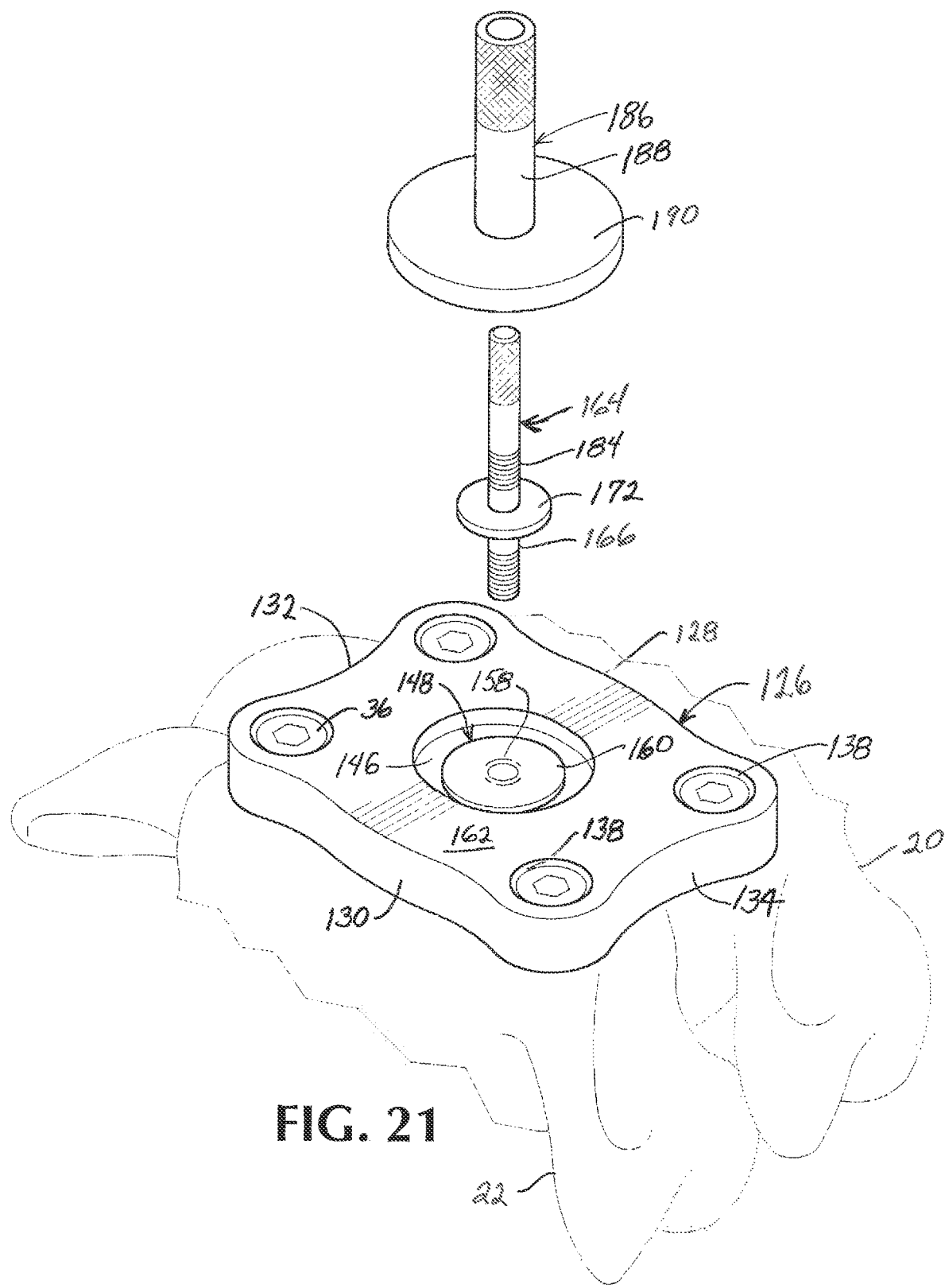
FIG. 21 is a view similar to FIG. 1 showing a vertebral fixation plate incorporating an attached mounting member.

Referring now to FIGS. 21-25, a cervical portion of a spine including two adjacent vertebrae 20, 22 is shown in FIG. 21, with a vertebral fixation plate system 124 that is another embodiment of the system disclosed in this application in place, immobilizing the two vertebrae 20, 22 with respect to each other.

A vertebral fixation plate 126 has a pair of opposite ends 128, 130, respectively facing in cephalad and caudal directions, and a pair of opposite lateral sides 132, 134. Fasteners such as screws 36 are mounted in respective receptacles 138 in the corners of the fixation plate 126, from which the fasteners extend through respective holes 140 in the fixation plate 126 into each of the vertebrae 20 and 22, as may be seen in FIGS. 23 and 24. A respective pair of the screws 36 connect each of the opposite ends 128, 130 of the vertebral fixation plate 126 to one of the vertebrae 20, 22. Ideally, each of the ends, 128, 130 extends only a short distance along the respective vertebra 20 or 22 to which it is fastened, in order to leave room for an adjacent fixation plate (not shown) should a fusion be desired at the adjacent level of the spine at a later date.

Figure 24:
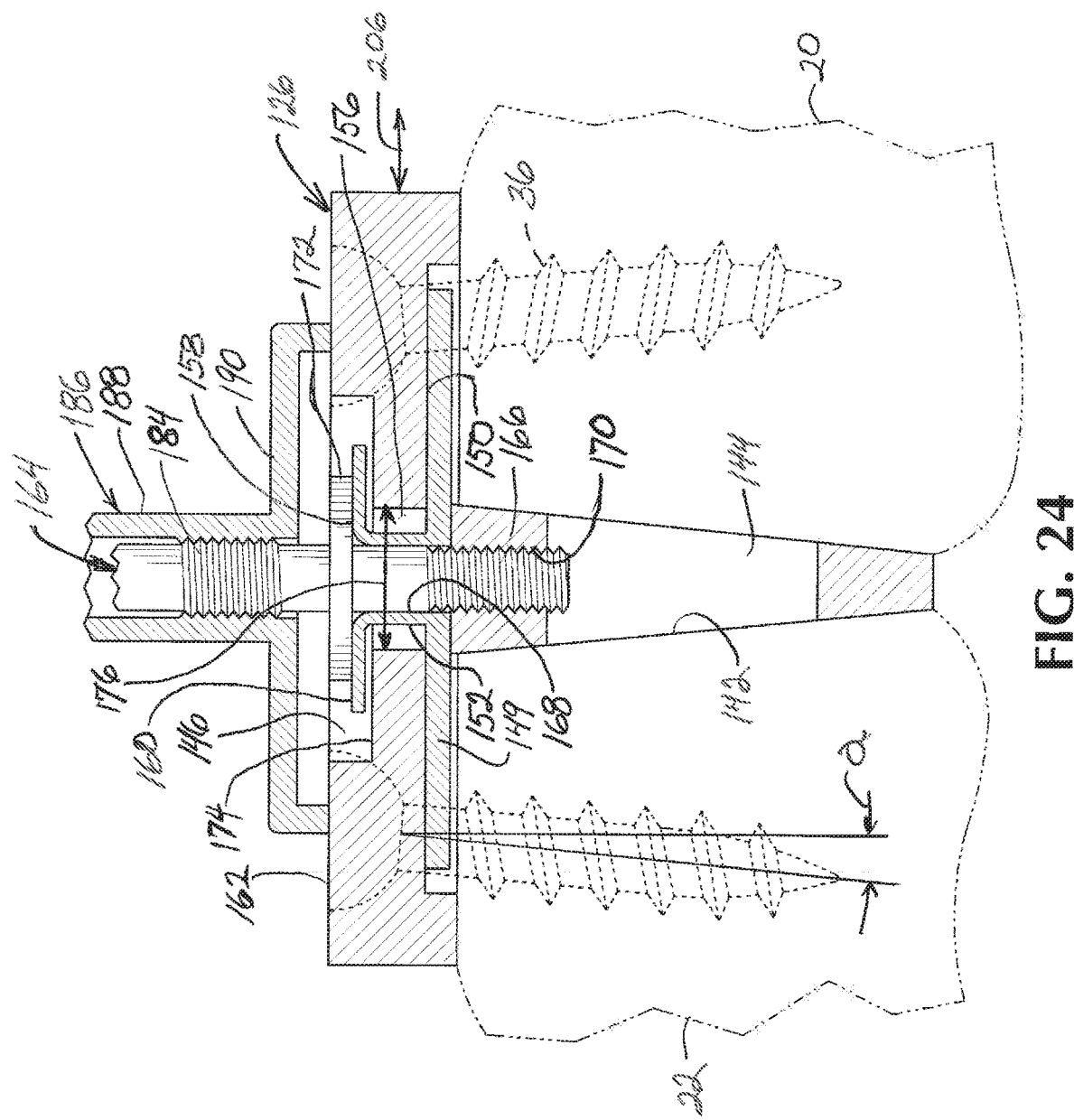
FIG. 24 is a sectional view taken along line 24-24 of FIG. 22A.

Each of the receptacles 138 may be bowl-shaped, or approximately hemispherical, and the respective hole 140 associated with each receptacle 138 and extending through the fixation plate 126 may be larger than the shaft of the screw 36 extending through the hole, so that the screw 36 may be oriented either perpendicular to the fixation plate 26 or at an angle α within a range of a few degrees from being perpendicular to the fixation plate 26, as seen in FIG. 24. This can simplify installation of the screws 36 and allow each of the screws 36 to be placed into a vertebra at a selected angle α intended to provide a secure attachment of the vertebral fixation plate 26 to the vertebra concerned and to provide improved security by virtue of the screws 136 not being parallel with each other.

As seen best in FIG. 24, the vertebral fixation plate 126 bridges the space 142, between the pair of adjacent vertebrae 20, 22, from which the natural intervertebral disc has been removed, and where an interbody fusion device 144, hereinafter at times called a graft body 144, has been installed.

In FIGS. 21-24 it may be seen that the front, or outer, face of the vertebral fixation plate 126 defines a centrally-located recessed area 146. A mounting member 148 has a main body portion 149 whose general shape is similar to that of a flat washer, with a thickness 182. The main body portion 149 of the mounting member 148 is located within a mounting member receptacle 150 in the intervertebral fixation plate 126. A tube 152 extends from the upper, or outer face 154 of the main body portion 149 of the mounting member 148, through an opening 156 that extends through the intervertebral fixation plate 126 into the mounting member receptacle 150. An inner face of the main body portion 149 is opposite the outer face. At the outer end 158 of the mounting member 148 the tube 152 is flared outward, forming a keeper flange 160 on the opposite, upper or outer side 162 of the intervertebral fixation plate 126. The keeper flange 160 is large enough to keep the mounting member 148 attached to the fixation plate 126 and may be located in the recessed area 146 in the outer face of the plate 126.

A fastener 164, which may be a specially designed screw, has a shaft 166 including a threaded distal end portion that can pass freely through the tube 152 and a central opening 168 through the main body 149 of the mounting member 148, at the base of the tube 152, which is located within the opening 156 through the vertebral fixation plate 126. The threaded end of the shaft 166 extends into and is mated in an internally threaded receptacle 170 in a front face of the graft body 144. The fastener 164 includes a radially-extending flange 172 located at an appropriate distance from the distal end of shaft 166 so that the flange 172 of the fastener 164 can be brought to bear against the retaining flange 160 at the flared outer end 158 of the tube 152 as the fastener 164 is screwed into the receptacle 170, to fasten the mounting member 148 tightly to the graft body 144.

Figure 23:
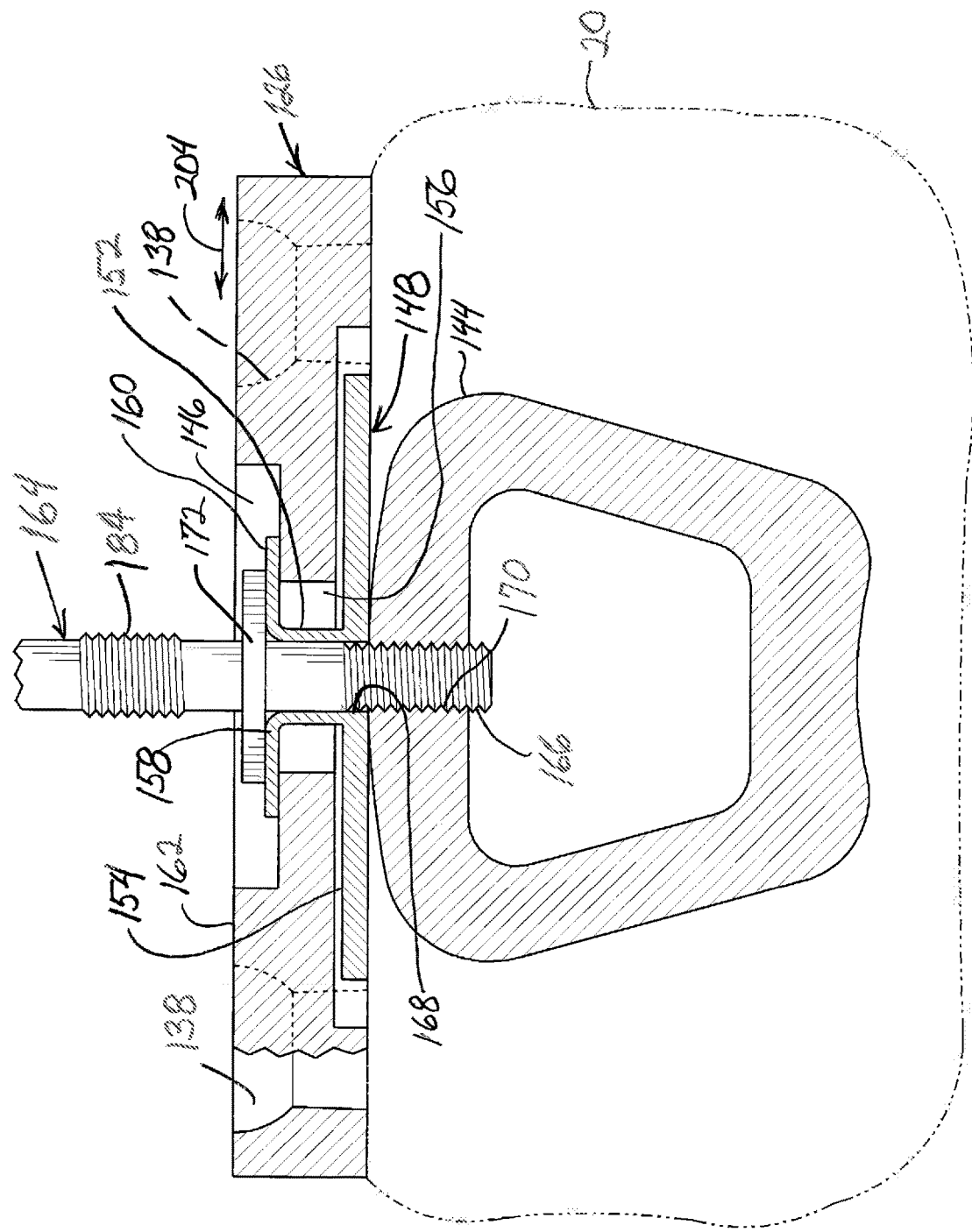
FIG. 23 is a sectional view taken along line 23-23 of FIG. 22A.

As shown in FIGS. 21, 23, and 24, the retaining flange 160 at the outer end 158 of the tube 152 extends radially within the recessed area 146 and may be in contact with a bottom surface 174 of the recessed area 146, keeping the vertebral fixation plate 126 attached to the mounting member 148. A transverse dimension 178 of the opening 156 is greater than the outer diameter of the tube portion 152 of the mounting member 148, and the bottom surface 174 of the recessed area 146 is larger than the flange 160, so that when the mounting member 148 is fastened to the graft body 144 the vertebral fixation plate 126 can be moved through a small distance with respect to the mounting member 148. Preferably, the respective sizes of the flange 160, the opening 156, and the recessed area 146 are related so that flange 160 prevents the vertebral fixation plate 126 from escaping from the mounting member 148 regardless of the location of the tube portion 152 of the mounting member 148 within the opening 156 through the vertebral fixation plate 126.

Figure 22A:
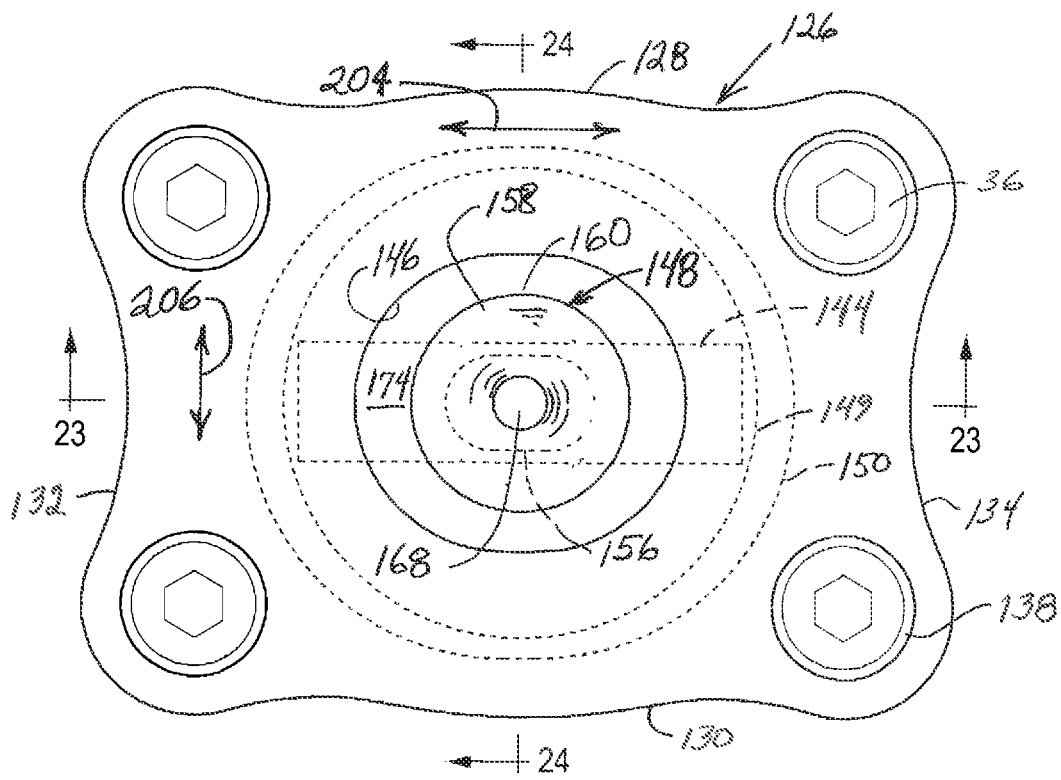
FIG. 22A is a plan view similar to FIG. 2, showing the vertebral fixation plate of FIG. 21.
Figure 22B:
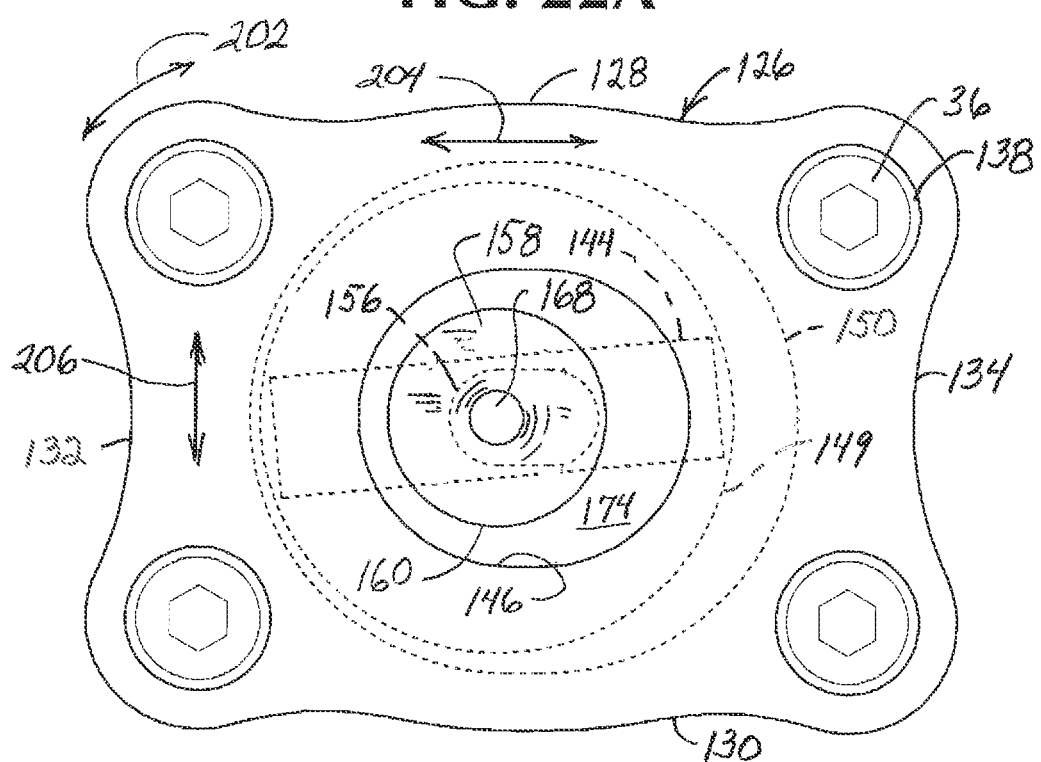
FIG. 22B is a plan view similar to FIG. 22A, but showing the vertebral fixation plate moved with respect to the attached mounting member.

The recessed area 146 and the opening 156 may be oval, allowing the vertebral fixation plate 126 to move a greater distance in a lateral direction than in a longitudinal direction with respect to the mounting member 148, or they may be of another shape, if desired, so long as there is space surrounding the flange 160 permitting the vertebral fixation plate 126 to be rotated about the mounting member 148 with respect to the graft body 144, as indicated by the arrow 178 in FIG. 22B.

Figure 25:
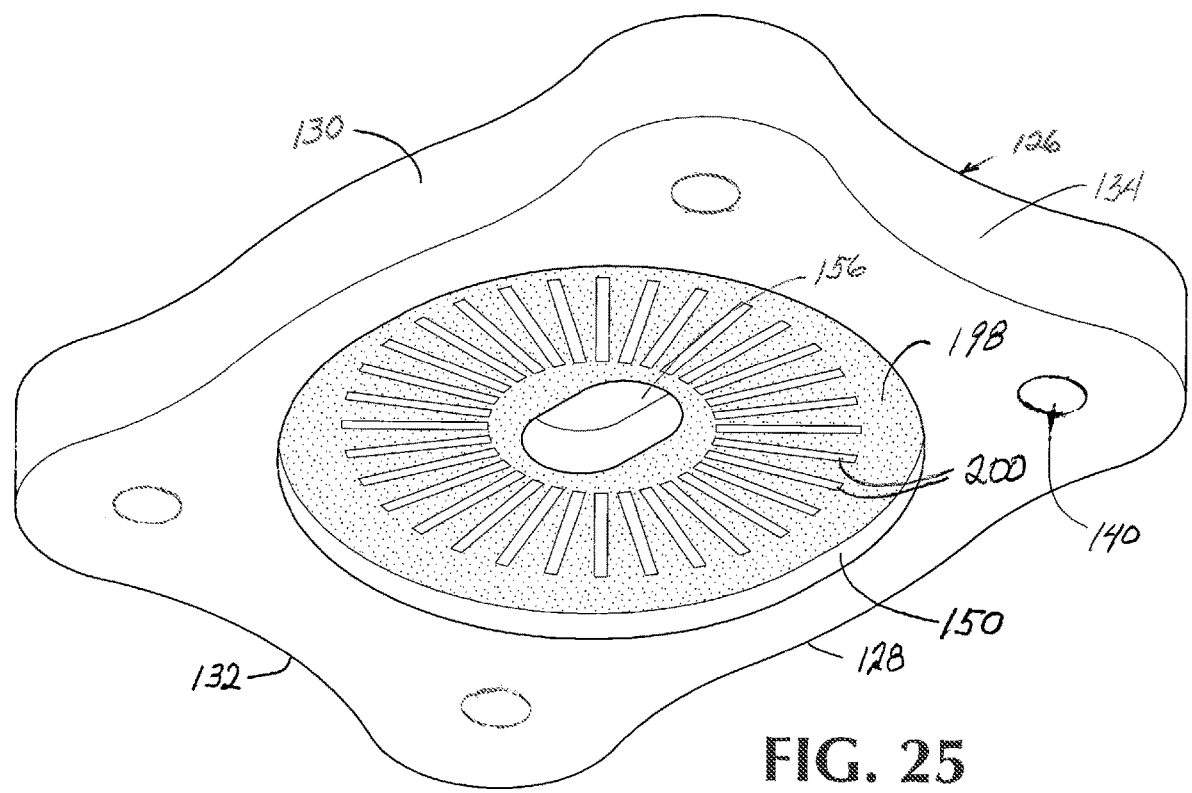
FIG. 25 is an exploded isometric view showing the inner side of a receptacle defined in the vertebral fixation plate shown in FIGS. 21-24 and also showing the mating surface of the mounting member normally located within the receptacle defined in the vertebral fixation plate when the mounting member is attached to the vertebral fixation plate as shown in FIGS. 21-24.
Figure 25:
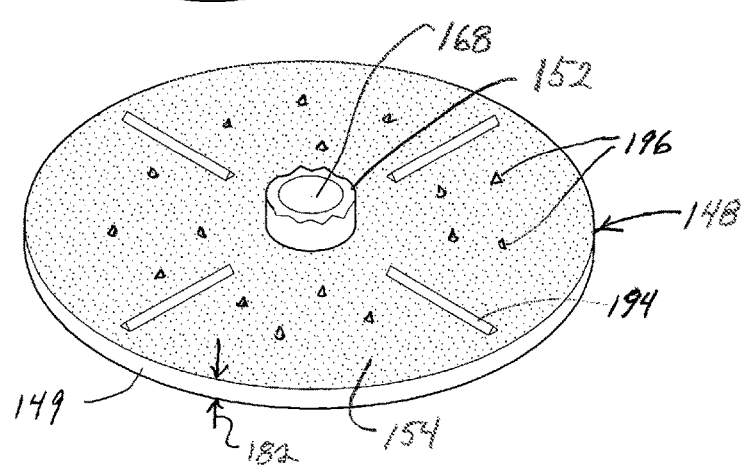

Referring to FIGS. 23, 24, and 25, the main body portion 149 of the mounting member 148 is located within a mounting member receptacle 150 defined in the inner side of the fixation plate 126, that is, the side of the fixation plate 126 facing toward the vertebrae 20, 22 and the graft body 144. The main body portion 149 of the mounting member is located adjacent the front face of the graft body 144 and is movable with respect to the vertebral fixation plate 126 through a distance limited by the size of the mounting member receptacle 150 or by the relative sizes of the tube 152 and the opening 156, or the relative sizes of retaining flange 160 and the recessed area 145. That is, the receptacle 150 is larger in its lateral and longitudinal dimensions than the corresponding dimensions of the mounting member 148. At the same time, however, the mounting member 148 is retained within the receptacle 150 so that the vertebral fixation plate 126 and the mounting member 148 can be handled as a unit during a vertebral fusion procedure.

The fastener 164 includes an externally threaded portion 184 spaced apart from the flange 172 in the direction opposite the threaded distal end of the shaft 166. A plate retainer 186 includes a tubular body portion 188 with internal threads that can engage the externally threaded portion 184 of the fastener 164. The plate retainer 186 includes a retainer, or pressing, flange 190 extending radially away from the distal end of the tubular body 188. The pressing flange 190 preferably has a diameter that is great enough to span the recessed portion 146 of the intervertebral fixation plate, and may have a depending outer rim to provide clearance for the flared outer end 158 of the tube 152. Tightening the plate retainer 186 along the fastener 164 and urging the pressing flange 190 against the outer side 162 of the vertebral fixation plate 126 with the shaft portion 166 of the fastener 164 extending through the tube 152 of the mounting member 148, as may be seen in FIG. 24, forces the interior or ceiling surface 198 of the receptacle 150 against the outer face 154 of the mounting member 148 and fixes the location of the vertebral fixation plate 126 with respect to the mounting member 144 and thus also with respect to the graft body 144 and the adjacent vertebrae 20 and 22.

The outer face 154 of the main body 149 of the mounting member 148 may be provided with a surface configuration adapted to resist relative movement and maintain the relative positions of the mounting member 148 and the vertebral fixation plate 126. For example, there may be a set of small ridges 194 radiating outwardly from the tube 152, as shown in a simplified view in FIG. 25, or small projecting points 196 may be provided. The recessed interior or ceiling surface 198 of the receptacle 150 for the mounting member 148, defined in the inner side of the vertebral fixation plate 126, may also be rough or may define shallow grooves 200 to receive the ridges 194 so as to retain the intervertebral fixation plate 126 at a selected one of a plurality of closely spaced angular positions with, for example, 3° separation, allowing for a total of angular adjustment through a range of as much as 30°. Overlapping sets of such grooves 200 (not shown) may also be provided in locations corresponding with translation of the intervertebral fixation plate 126 by small distances with respect to the mounting member 148. For example, it may be desirable to provide for a total available distance for translational adjustment of about 8 mm in the lateral direction of arrow 204 and about 6 mm in the longitudinal direction of arrow 206. Also, closely spaced small pits may be provided in the ceiling 190 to receive the points 196 to keep the vertebral fixation plate 126 stationary in a selected location and orientation with respect to the mounting member 148 and the vertebrae 20 and 22. In preparation for installation of the screws 36, the intervertebral fixation plate 126 is pressed against the mounting member 148 by tightening the retainer 186 along the threaded portion 184 of the fastener 164 so that the retainer flange 190 pushes the vertebral fixation plate 126 against the mounting member 148. This will bring the raised ridges 194 or points 196 on the outer face 149 of the mounting member 148 into engagement with respective ones of the grooves 200 or pits defined in the adjacent interior or ceiling surface 198 of the receptacle 180.

Since the vertebral fixation plate 126 is attached to the mounting member 148, a surgeon performing a vertebral fusion procedure can install the graft body 144 between the vertebrae 20, 22 to be fused and thereafter can install the mounting member 148 and the vertebral fixation plate 126 as a unit. Tightening the fastener 164 into the graft body 144 attaches the mounting member securely and in a fixed location on the graft body 144. The intervertebral fixation plate 126 can then be placed in what the surgeon estimates to be the required location and orientation with respect to the vertebrae to be fused and can be held there by screwing the plate retainer 186 down so that the pressing retainer flange 190 pushes the vertebral fixation plate 126 against the mounting member 148. The location and orientation of the vertebral fixation plate 126 can be adjusted if necessary after a radiographic check, as explained above. The plate retainer 186 can then be re-tightened to maintain the desired relationship between the vertebral fixation plate 126 and the vertebrae 20 and 22 while the screws 36 are installed through the vertebral fixation plate to fasten it to the vertebrae. For example, the fixation plate 126 has been moved from an initial position shown in FIG. 22A to an adjusted position shown in FIG. 22B. Once the screws 36 are installed the fastener 164 and the plate holder 184 can be removed and the surgeon can close the patient.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A vertebral fixation plate system for use with an interbody fusion device having a front face, the system comprising:

(a) a vertebral fixation plate having a principal plane, an inner face, an outer face, and a thickness and defining a plurality of primary fixation fastener receptacles each located in a respective position to receive a respective fastener extending therethrough into one of a pair of adjacent vertebrae to be held in a fixed positional relationship to each other, the vertebral fixation plate also defining a recessed mounting member receptacle in the inner face;

(b) a mounting member, the mounting member having a main body and a tube extending to an outer end of the mounting member, the main body having an outer face and an inner face and being located within the recessed mounting member receptacle, the tube being outwardly flared at the outer end of the mounting number, thus including a retaining flange, and the tube having a bore extending from the inner face of the main body portion and through the main body and the retaining flange at the outer end;

(c) the recessed mounting member receptacle having a ceiling and a depth and the recessed mounting member receptacle having dimensions, in respective directions generally parallel with the principal plane of the vertebral fixation plate, at least great enough so that the main body of the mounting member is free to move within the mounting member receptacle, through at least a predetermined distance generally parallel with the principal plane of the vertebral fixation plate;

(d) the vertebral fixation plate defining an opening extending through the vertebral fixation plate into the mounting member receptacle, the tube of the mounting member extending from the outer face of the main body through the opening to the outer end, the retaining flange being larger than the opening, and the mounting member thereby being attached to the vertebral fixation plate; and (e) the outer face of the main body of the mounting member and the ceiling of the mounting member receptacle having respective interlocking surface configurations that are capable of engaging each other, configured to interlock the vertebral fixation plate in a selected one of a plurality of predefined locked positions relative to the mounting member, so as to resist movement of the vertebral fixation plate relative to the mounting member, at least a portion of the plurality of pre-defined locked positions having different angular orientations with respect to each other.

2. The system of claim 1 wherein the outer face of the vertebral fixation plate includes a recessed portion having a bottom surface surrounding the opening extending through the vertebral fixation plate.

3. The system of claim 2 further including a fastener having a shaft portion slender enough to extend freely through the bore of the tube of the mounting member and long enough to extend beyond the main body portion of the mounting member into a fastener receptacle in a front face of an interbody fusion device, the fastener having a flange extending radially outward from the shaft portion, the flange being in contact with the outer end of the mounting member when the shaft portion extends into the fastener receptacle.

4. The system of claim 1 further including a fastener having a shaft portion slender enough to extend freely through the bore of the tube of the mounting member and long enough to extend beyond the main body portion of the mounting member and matingly into a fastener receptacle in a front face of an interbody fusion device, the fastener having a flange extending radially outward from the shaft portion and in position to be brought into contact against the outer end of the mounting member when the shaft portion extends into the fastener receptacle.

5. The system of claim 1 wherein the interlocking surface configuration of the outer face of the main body of the mounting member includes a plurality of projecting ridges and wherein the ceiling of the mounting member receptacle defines a plurality of closely-spaced small grooves adapted to receive the projecting ridges and resist movement of the vertebral fixation plate relative to the mounting member when the vertebral fixation plate is in a desired location and orientation relative to the mounting member.

6. The system of claim 1 wherein the mounting member and the vertebral fixation plate are connected with each other but movable with respect to each other.

7. The system of claim 1 including a fastener having a shaft portion extending through the mounting body and matingly engaged in the interbody fusion device, the system also having a plate retainer extending radially from the shaft portion of the fastener and arranged to be moved along the shaft portion of the fastener, the plate retainer including a pressing flange arranged to be placed into contact against the outer face of the vertebral fixation plate.

8. The system of claim 2 wherein the outer end of the mounting member is located in the recessed portion of the outer face of the vertebral fixation plate.

9. The system of claim 6 wherein the retaining flange of the outer end of the mounting member is located in a recessed portion of the outer face of the vertebral fixation plate.

10. The system of claim 1 further including a fastener having a shaft portion slender enough to extend freely through the bore of the tube of the mounting member and adapted to extend matingly into a fastener receptacle in a front face of an interbody fusion device, the system also including a plate retainer engaged with the fastener, the plate retainer including a pressing flange extending radially away from the fastener, and the plate retainer being adjustably movable along the fastener and into contact against the vertebral fixation plate, when the shaft portion of the fastener extends matingly into the fastener receptacle, so as to urge the ceiling of the recessed mounting member receptacle against the outer face of the main body portion of the mounting member and thereby to fix the location of the vertebral fixation plate with respect to the mounting member and thus also with respect to the interbody fusion device.

* * * * *